US008357728B2

(12) United States Patent
Butler et al.

(10) Patent No.: US 8,357,728 B2
(45) Date of Patent: Jan. 22, 2013

(54) POROUS MATERIAL AND METHOD OF PRODUCTION THEREOF

(75) Inventors: Rachel Butler, Durham (GB); Andrew Ian Cooper, Liverpool (GB)

(73) Assignee: IOTA NanoSolutions Limited, London (GB)

( * ) Notice: Subject to any disclaimer, the term of this patent is extended or adjusted under 35 U.S.C. 154(b) by 1179 days.

(21) Appl. No.: 10/566,873

(22) PCT Filed: Jul. 29, 2004

(86) PCT No.: PCT/GB2004/003264
§ 371 (c)(1),
(2), (4) Date: Jul. 3, 2006

(87) PCT Pub. No.: WO2005/014704
PCT Pub. Date: Feb. 17, 2005

(65) Prior Publication Data
US 2007/0135528 A1    Jun. 14, 2007

(30) Foreign Application Priority Data
Aug. 4, 2003 (GB) .................................. 0318182.3

(51) Int. Cl.
*C08J 9/00* (2006.01)
*C08J 9/28* (2006.01)

(52) U.S. Cl. ............................... 521/64; 521/50; 521/61

(58) Field of Classification Search .................... 521/64, 521/61
See application file for complete search history.

(56) References Cited

U.S. PATENT DOCUMENTS

| 3,579,360 | A | 5/1971 | Rey |
| 2003/0064156 | A1 | 4/2003 | Shih et al. |
| 2003/0134918 | A1* | 7/2003 | Ko et al. ........................ 521/50 |

FOREIGN PATENT DOCUMENTS

| GB | 217 587 | 11/1924 |
| GB | 2 099 315 | 12/1982 |
| GB | 2399084 | 9/2004 |
| WO | 00/46281 | 8/2000 |
| WO | 01/25390 | 4/2001 |
| WO | 02/09678 | 2/2002 |

(Continued)

OTHER PUBLICATIONS

Butler, Rachel, Cait M. Davies, and Andrew I Cooper. "Emulsion Templating Using High Internal Phase Supercritical Fluid Emulsions." Advanced Materials. 2001, vol. 13, Part 19, Oct. 2. pp. 1459-1463.*

(Continued)

*Primary Examiner* — Randy Gulakowski
*Assistant Examiner* — Kara Boyle
(74) *Attorney, Agent, or Firm* — Michael Best & Friedrich LLP

(57) ABSTRACT

The present invention relates to a method for producing a porous material comprising the steps of; (a) providing a C/W emulsion comprising an aqueous phase, a matrix building material, a surfactant and liquid $CO_2$ phase; (b) at least partially freezing the aqueous phase; (c) gasifying $CO_2$ from the liquid $CO_2$ phase to form an intermediate porous material; (d) venting gasified $CO_2$ from the intermediate porous material; and (e) freeze drying the intermediate porous material at least substantially to remove the aqueous phase and form the porous material. The present invention also relates to a porous material obtainable by the method.

24 Claims, 13 Drawing Sheets

FOREIGN PATENT DOCUMENTS

WO 2004/011537 2/2004

OTHER PUBLICATIONS

International Search Report Application No. PCT/GB2004/003264 mailed Oct. 22, 2004.

Hainey et al., Synthesis and Ultrastructural Studies of Styrene-Divinylbenzene Polyhipe Polymers, Macromolecules, 1991, 24, pp. 117-121.

Barbetta et al., High internal phase emulsions (HIPEs) containing divinylbenzene and 4-vinylbenzyl chloride and the morphology of the resulting PolyHIPE materials, Chem. Commun., 2000, pp. 221-222.

Cooper, Porous Materials and Supercritical Fluids, Advanced Materials, Jul. 4, 2003, 15, pp. 1049-1059.

Goel et al., Generation of Microcellular Polymeric Foams Using Supercritical Carbon Dioxide. II: Cell Growth and Skin Formation, Polymer Engineering and Science, Jul. 1994, 34, pp. 1148-1156.

Wood et al., Synthesis of Macroporous Polymer Beads by Suspension Polymerization Using Supercritical Carbon Dioxide as a Pressure-Adjustable Porogen, Macromolecules, 2001, 34, pp. 5-8.

Hebb et al., Structural Control in Porous Cross-Linked Poly(methacrylate) Monoliths Using Supercritical Carbon Dioxide as a "Pressure-Adjustable" Porogenic Solvent, Chem. Mater., 2003, 15, pp. 2061-2069.

Howdle et al., Supercritical fluid mixing: preparation of thermal sensitive polymer composites containing bioactive materials, Chem. Commun., 2001, pp. 109-110.

Zhang et al., Synthesis of Monodisperse Emulsion-Templated Polymer Beads by Oil-in-Water-Oil (O/W/O) Sedimentation Polymerization, Chem. Mater., 2002, 14, pp. 4017-4020.

Cameron et al., High Internal Phase Emulsions (HIPEs)—Structure, Properties and Use in Polymer Preparation, Advances in Polymer Science, 1996, 126, pp. 163-214.

Ruckenstein, Concentrated emulsion polymerization, Advances in Polymer Science, 1997, 127, pp. 1-58.

Chen et al., A hybrid network of synthetic polymer mesh and collagen sponge, Chem. Commun., 2000, pp. 1505-1506.

Chen et al., Hybrid Biomaterials for Tissue Engineering: A Preparative Method for PLA or PLGA—Collagen Hybrid Sponges, Advanced Materials, 2000, 12, pp. 455-457.

Yokoyama et al., Morphology and structure of highly elastic poly(vinyl alcohol) hydrogel prepared by repeated freezing-and-melting, Colloid and Polymer Science, 1986, 264, pp. 595-601.

Chen et al., Preparation of poly(L-lactic acid) and poly(DL-lactic-co-glycolic acid) foams by use of ice microparticulates, Biomaterials, 2001, 22, pp. 2563-2567.

Park et al., Characterization of porous collagen/hyaluronic acid scaffold modified by 1-ethyl-3-(3-dimethylaminopropyl)carbodiimide cross-linking, Biomaterials, 2002, 23, pp. 1205-1212.

Whang et al., A novel method to fabricate bioabsorbable scaffolds, Polymer, 1995, 36, pp. 837-842.

Cooper et al., Synthesis of Highly Cross-Linked Polymers in Supercritical Carbon Dioxide by Heterogeneous Polymerization, Macromolecules, 1999, 32, pp. 2156-2166.

Cooper et al., Synthesis of Well-Defined Macroporous Polymer Monoliths by Sol-Gel Polymerization in Supercritical $CO_2$, Ind. Eng. Chem. Res., 2000, 39, pp. 4741-4744.

\* cited by examiner

POROUS MATERIAL AND METHOD OF PRODUCTION THEREOF

This patent application is a national stage filing under 35 U.S.C. 371 of International Application No. PCT/GB2004/003264, filed on Jul. 29, 2004, which claims the benefit of priority to United Kingdom Patent Application No. 0318182.3, filed on Aug. 4, 2003. Priority to each application is hereby claimed.

The present invention relates to the production of porous materials from $CO_2$-in-water (C/W) emulsions.

Porous materials have been used in a variety of applications and have proved especially useful in the biomedical field, for example, as label or sensing-device carriers, affinity chromatography agents, for the immobilisation of enzymes, as supports for tissue engineering, and in drug delivery. Porous polymeric materials can be produced by a number of methods and can result in materials with quite different physical attributes which are suited to a particular application.

It is often preferable to have a material with an internal structure that is extremely porous. Certain porous polymeric materials can be produced using high internal phase emulsions (HIPEs), which are emulsions where the volume percentage of the internal phase is typically greater than 74.05% (P. Hainey, et al., Macromolecules 1991, 24, 117; N. R. Cameron, et al. Adv. Polym. Sci. 1996, 126, 163; A. Barobtainta, et al., Chem. Commun., 2000, 221). The structure produced from a HIPE, is often referred to as a 'templated structure' and this type of structure is most desirable. Materials can be templated by polymerization of oil-in-water (O/W) HIPEs but the techniques utilising them are extremely solvent intensive because the internal oil phase (often an organic solvent) can constitute between 75 and 90% of the total reaction volume. The use of such solvents may leave residues on the material, which is undesirable for certain applications (for example in the biomedical field). Furthermore, it is not possible to produce water-soluble materials via this method because the products are typically highly cross-linked and therefore water-insoluble.

Butler, R. et al., (2001) (Adv. Mater., 2001, 13, 1459-1463) discloses a method of producing porous monolithic type structures involving $CO_2$-in-water (C/W) templating and requires a chemical reaction between monomers (e.g., acrylamide and methylene bisacrylamide) to lock in the structure of the C/W emulsion, and thus to form porous monolithic type structures. The resultant materials are cross-linked which limits the scope of application for materials produced by this process. For example, these highly cross-linked materials cannot be redissolved in water or in organic solvents. This process also requires an elevated temperature in order to initiate the reaction and therefore this process is unsuitable for use with thermally sensitive materials. Furthermore, the increased temperatures are undesirable as they give rise to a destabilisation of the emulsion and can denature any active ingredient added to the emulsion.

Other methods to produce porous materials utilising carbon dioxide have been disclosed, as reviewed in A. I. Cooper, Adv. Mater., 2003, 15, 1049-1059. Goel, et al., (1994) (Polym. Eng. Sci., 1994, 34, 1148-1156) discusses the use of $CO_2$ to foam polymeric materials by expansion. Cooper, et al., (2001) and (2003) (Macromolecules, 2001, 34, 5-8 and Chem. Mater., 2003, 15, 2061-2069) discuss a reaction-induced phase separation method for the production of porous beaded and monolithic materials using $CO_2$. Both of these processes give rise to significantly different porous morphologies to those produced using an emulsion templating method, and are applicable to particular restricted classes of materials. Foaming by expansion with $CO_2$ is limited to polymers that can melt at moderate temperatures or that are highly plasticized by $CO_2$ (S. M. Howdle, et al., Chem. Commun., 2001, 109). By contrast, reaction induced phase separation in $CO_2$ can be used to form rigid, 'solvent-free' materials that cannot be foamed, but the technique is limited to materials that can be produced by the reaction of $CO_2$-soluble precursors (Cooper and Holmes, International Patent Publication No. WO 00/46281).

Zhang and Cooper (2002) (Chem. Mater., 2002, 14, 4017-4020) disclose the synthesis of HIPE-templated beads by using either organic solvents or mineral oils as the internal phase. This method has drawbacks: for example, removal of the internal 'oil' phase is very difficult and requires large volumes of organic solvent both as the internal phase and in the subsequent purification steps. The materials produced by this method are highly cross-linked and thus substantially insoluble in water or in organic solvents.

UK Patent Application No. 02099315.1 discloses a HIPE-templated porous polymer material and a method of production thereof, where a large majority, for example 80% or more, or even up to about 100% of the material is in the form of substantially spherical beads with narrow bead size distributions. These polymeric beads have a porous structure, characterized by cavities joined by interconnecting pores (a HIPE structure), some of which are connected to the surface of the bead. The materials produced by this method are highly cross-linked and thus insoluble. UK Patent Application No. 0217587.5 discusses porous beads and methods of producing them and in particular to a method of producing hydrophilic polymeric beads by freeze-drying a droplet containing a polymeric material in a continuous phase of an oil-in-water (O/W) emulsion is disclosed. This method uses a large volume of a volatile organic solvent (e.g., cyclohexane) as the template phase.

It is an object of the present invention to address one or more of the problems associated with the prior art materials. It is a further object of the present invention to provide a highly porous material which has a 'templated' structure, which is produced by a substantially non-toxic process which preferably does not utilise any organic solvents (i.e., volatile organic compounds, VOCs) or involatile oils. It would be advantageous to provide a porous material that can be produced without the addition of chemical initiators or monomers. It would also be advantageous to produce the material in a moulded, monolithic form. Furthermore, it would be desirable to produce a material that is substantially water-soluble. Another object of the present invention is to produce a porous material that allows for incorporation of active species without any substantial denaturation, degradation, or attenuation of the active species.

In accordance with the present invention, there is provided a method for producing a porous material comprising the steps of:

(a) providing a C/W emulsion comprising an aqueous phase, a matrix building material, a surfactant and a liquid $CO_2$ phase;

(b) at least partially freezing the aqueous phase;

(c) gasifying $CO_2$ from the liquid $CO_2$ phase to form an intermediate porous material;

(d) venting the gasified $CO_2$ from the intermediate porous material; and (e) freeze drying the intermediate porous material at least substantially to remove the aqueous phase and form the porous material.

The method in accordance with the present invention has significant advantages over techniques currently in use due to the elimination of organic solvent residues, high pore volumes, the ability to form porous structures from rigid materials that cannot be foamed by expansion, and the incorporation of active species without substantial denaturation, degradation, or attenuation of the active species. Furthermore, all of the materials used in the method can be selected to have low toxicity profiles in addition to being biodegradable. Additionally, the method does not require the addition of any chemical initiators or monomers and substantially no internal phase residue is left in the material, which is very difficult to achieve using conventional emulsion templating methods.

Accordingly, the invention provides a porous material comprising a water-soluble polymeric matrix, which matrix comprises substantially no residual organic solvent.

The porous material of the invention is obtainable by a method which utilises substantially no organic solvent and hence the matrix is free from any residual organic solvent component.

Preferably, the porous material of the invention comprises surfactant moieties entangled with the polymeric matrix. The presence of such surfactant moieties may result from the formation of the porous material of the invention from a C/W emulsion comprising the surfactant moieties.

The matrix building material may comprise a number of materials. The matrix building material may comprise a polymeric material. The polymeric material will preferably be substantially free of cross-linking. Such a polymeric material may be a synthetic polymer material or a natural polymer material. Preferably, the matrix building material is a vinyl polymer. More preferably, the matrix building material is selected from one or more of the following materials: poly (vinyl alcohol), dextran, sodium alginate, poly(aspartic acid), poly(ethylene glycol), poly(ethylene oxide), poly(vinyl pyrrolidone), poly(acrylic acid), poly(acrylic acid)-sodium salt, poly(acrylamide), poly(N-isopropyl acrylamide), poly(hydroxyethyl acrylate), poly(acrylic acid), poly(sodium styrene sulfonate), poly(2-acrylamido-2-methyl-1-propanesulfonic acid), polysaccharides, and cellulose derivatives. Other water-soluble polymers, copolymers, or derivatives of such materials will be apparent to those skilled in the art. The matrix building material may additionally be substantially water-soluble or at least the major constituent of the material may be water-soluble. The matrix building material may also be contained in any one of the constituents of the emulsion, but it is preferably contained within the aqueous phase.

The emulsion may further comprise a dopant, which is preferably contained within the aqueous or $CO_2$ phase. A number of dopants may be used to generate a wide range of materials and these will be apparent to those skilled in the art. Preferably, the dopant is substantially water-soluble. The water-soluble dopant may be added with the purpose of delivering this additive into an aqueous solution upon dissolution of the emulsion-templated material. The water-soluble dopant may be selected from a very wide range of substantially water-soluble or water-dispersible materials and such dopants will be apparent to one skilled in the art. Preferably, a dopant is selected from one or more of the following dopants: pharmaceutical actives, pharmaceutical salts, enzymes, dyes, oxidising agents, reducing agents, cleaning agents, reagents for organic synthesis, agrochemicals, fabric softeners, clothes care agents, bleaches, flavours, fragrances, vitamins or nutraceuticals, metal nanoparticles (e.g., metal hydrosols), inorganic nanoparticles, biological polymers (e.g., DNA, RNA), growth factors and growth co-factors and live cells (e.g., stem cells).

A substantially water-soluble inorganic or organic additive may be dissolved in the aqueous continuous phase in order to enhance the strength of the polymer beads or to form a highly porous inorganic skeleton after subsequent dissolution of the organic polymer or by calcination of the organic at elevated temperatures. A number of water-soluble structural additives may be used. Preferably, a water-soluble structural additive is selected from one or more of the following additives: partially hydrolysed silica precursors (i.e., a silica 'sol'), other alkoxide sols, hydroxyapatite salts, and sodium silicate. The substantially water-soluble inorganic or organic additive may be in addition to a dopant or in place of a dopant.

The temperature of the emulsion may be reduced to a temperature that allows the emulsion to become frozen and it will be evident that the precise temperature will be dependent upon the elements that comprise the emulsion. The aqueous phase of the emulsion is typically frozen by immersion in a bath of acetone and solid carbon dioxide, although other methods of cooling will be apparent to those skilled in the art. Preferably, the temperature will not be reduced to less than $-56°$ C. as this is the melting point of $CO_2$. More preferably, the temperature of the emulsion will be reduced to a temperature in the range of $-5°$ C. to $-30°$ C. Most preferably, the temperature of the emulsion will be reduced to a temperature in the range of $-15°$ C. to $-25°$ C. Once the aqueous phase is frozen, the structure becomes 'locked' in place. Subsequent removal of the internal $CO_2$ droplet phase in the emulsion is easily achieved as the $CO_2$ reverts to the gaseous state on depressurization of the system, leaving behind a frozen, porous monolithic block which is a skeletal replica of the emulsion immediately prior to the onset of freezing. Removal of the aqueous phase via freeze drying allows the isolation of a solid porous material which retains this structure. This structure is not formed by expansion of the polymer (i.e., the structure is not an expanded foam) because the rigid frozen structure does not expand appreciably during venting of the liquid $CO_2$.

It will be apparent to one skilled in the art that a number of surfactants may be utilised to obtain the porous material. The surfactants used will be dependent upon the application for which the porous material will be used but will generally be one which is capable of stabilizing a concentrated $CO_2$-in-water (C/W) emulsion, taking into account any other constituents (e.g., polymers, dopants) in the aqueous or the $CO_2$ phase. The presence of a polymer or dopant in the aqueous phase may substantially affect the stability of the emulsion with respect to an equivalent emulsion formed from $CO_2$ and pure water. Preferably, the surfactant is selected from one or more of the following list of surfactants: CTAB (cetyltrimethylammonium bromide), SDS (sodium dodecyl sulphate), pluronic surfactants, Brij 30 and Tween 40. Most preferably, the surfactant should be CTAB. Commonly, the porous material may be produced in the form of a monolithic block. Alternatively, the concentrated liquid $CO_2$-in-water emulsion may be sprayed directly into a suitable refrigerant (e.g., liquid nitrogen, liquid ammonia, liquified noble gas such as argon, liquefied chlorinated hydrocarbon such as trichloroethylene, chlorofluorocarbon, freon, hexane, dimethylbutene, isoheptane) in order to obtain porous particles.

Preferably, the constituents of the emulsion are in the following quantities: the matrix building material is in the range of 1-50% w/v and the surfactant is in the range of 0.1-20% w/v in respect of $H_2O$ and the $CO_2$ is in the range of 10-98% v/v. More preferably, the constituents of the emulsion are in the following quantities: the matrix building material in the range of 5-25% w/v and the surfactant is in the range of 0.5-15% w/v in respect of $H_2O$ and the $CO_2$ is in the range of 70-90% v/v. Most preferably, the constituents of the emulsion are in the following quantities: the matrix building material in the range of 10-20% w/v and the surfactant is in the range of 1-10% w/v in respect of $H_2O$ and the $CO_2$ is in the range of 75-85% v/v.

The emulsion may further comprise an active ingredient for incorporation into the porous material. A number of active ingredients for incorporation into the porous material will be apparent to the skilled addressee and such ingredients will be related to the function that the porous material is intended to perform. Preferably, the active ingredient is selected from one or more from the following group; pharmaceutical actives, pharmaceutical salts, enzymes, dyes, oxidising agents, reducing agents, cleaning agents, reagents for organic synthesis, agrochemicals, fabric softeners, clothes care agents, bleaches, flavours, fragrances, vitamins or nutraceuticals, metal nanoparticles (e.g., metal hydrosols), inorganic nanoparticles, biological polymers (e.g., DNA, RNA), growth factors/cofactors, and live cells (e.g., stem cells). Water-soluble additives can be used singly or as mixtures. As the method does not utilise elevated temperatures in the production of the porous material, the active ingredients are less likely to undergo denaturation and will remain fully active and therefore, the material is suited to a wide range of applications.

In accordance with yet another aspect of the present invention, there is provided a porous material obtainable by the method as herein described above. The porous material may be used for one or more of the following applications: biomaterials, food materials, tissue scaffolding. DNA storage, absorbents, controlled release matrices, scaffolds for sensor materials, wound-healing matrices, agrochemical release, reagent release (e.g., for chemical reactions), scaffolds for combinatorial chemistry, molecular separations, and diagnostic reagent release.

In accordance with another aspect of the present invention, there is provided a water-soluble porous material produced by the method as herein described comprising, a median pore diameter within the range of 5-100 microns, a total pore volume in the range of 8-15 $cm^3/g$ when approximately 80% v/v $CO_2$ is used as the template phase. It will be appreciated by one skilled in the art that lower pore volumes can be achieved by using less $CO_2$ in the templating procedure. Bulk densities of the emulsion-templated materials are typically in the range 0.02-0.06 $g/cm^3$, although higher densities can be achieved by using less $CO_2$ in the templating procedure. Preferably, the porous material will have a median pore diameter within the range of 15-55 microns. Materials produced without the $CO_2$ emulsion template have much lower levels of porosity (1.8-3.4 $cm^3/g$) and much smaller pores (4-6 microns). The emulsion-templated materials are much more highly porous than the equivalent non-emulsion-templated analogues. A water-soluble porous material obtainable by the method as herein above described may further be characterised by having substantially no solvent residue remaining in the material that arises from the internal template phase. The water-soluble porous material may additionally be characterised by being produced in the form of a moulded, monolithic block that substantially conforms to the shape of the vessel in which it is produced.

A method according to the present invention will now be illustrated by way of example only and with reference to the Figures in which.

Figure 1:
FIG. 1 is an electron micrograph at three different magnifications of a porous material produced in Sample 1 in accordance with the present invention.
Figure 1:
Figure 1:

An experiment was conducted in order to investigate the internal structural properties of porous materials produced from a stable C/W emulsions.

Emulsions comprising water, a polymer matrix building material (e.g., dextran) and a surfactant were produced with differing constituents. In addition to this, liquid $CO_2$ was also added to a number of emulsions in order to assess the effect on the $CO_2$ in producing internal structures as compared to porous materials produced without $CO_2$. All emulsions were produced with either dextran (Samples 1-18) or poly(vinyl alcohol) (PVA) (Samples 19-21) as the matrix building material in the aqueous phase of the emulsion. The emulsions were continuously stirred at 550 rpm for 45 min and were subsequently frozen at −20° C. The emulsions were then depressurised in order to allow the $CO_2$ to revert to the gaseous state and to produce a porous material. The material was subsequently dried by freeze drying for 48 hours or until all of the water was removed.

The following table shows the results of the experiments conducted which produced 21 different samples of porous material.

| Polymer | | CO$_2$/H$_2$O (v/v) | Polymer Concn. (w/v) | Surfactant | Surfactant Concn. (w/v) | Vol. of material (cm$^3$) | Intrusion Vol. (cm$^3$/g) | Med. Pore Diam. (microns) | Bulk density (g/cm$^3$) | Dopant molecule |
|---|---|---|---|---|---|---|---|---|---|---|
| 1 | Dextran | 0/100 | 14 | CTAB | 0 | 2.71 | 2.13 | 4.07 | 0.30 | None |
| 2 | Dextran | 0/100 | 14 | CTAB | 2 | 3.34 | 1.8 | 4.83 | 0.37 | None |
| 3 | Dextran | 0/100 | 14 | CTAB | 20 | 2.71 | 3.43 | 6.1 | 0.20 | None |
| 4 | Dextran | 80/20 | 8 | CTAB | 20 | 10.56 | 9.33 | 41.98 | 0.09 | None |
| 5 | Dextran | 80/20 | 8 | CTAB | 11 | 10.56 | 11.68 | 18.68 | 0.06 | None |
| 6 | Dextran | 80/20 | 14 | CTAB | 11 | 10.56 | 11.64 | 26.16 | 0.06 | None |
| 7 | Dextran | 80/20 | 14 | CTAB | 2 | 11.5 | 14.22 | 15.24 | 0.05 | None |
| 8 | Dextran | 80/20 | 14 | CTAB | 20 | 9.3 | 7.94 | 55.22 | 0.06 | None |
| 9 | Dextran | 80/20 | 14 | CTAB | 11 | 9.93 | 11.32 | 59.5 | 0.03 | None |
| 10 | Dextran | 80/20 | 14 | CTAB | 2 | 7.42 | 10.73 | 23.85 | 0.07 | None |
| 11 | Dextran | 80/20 | 14 | CTAB | 2 | 10.56 | 11.14 | 17.54 | 0.07 | None |
| 12 | Dextran | 80/20 | 14 | CTAB | 2 | 4.28 | 8.9 | 14.59 | | Ferrocene |
| 13 | Dextran | 80/20 | 14 | CTAB | 2 | 5.85 | 8.51 | 15.67 | 0.05 | Naproxen |
| 14 | Dextran | 80/20 | 14 | CTAB | 2 | 5.85 | 6.33 | 7.66 | 0.11 | AIBN |
| 15 | Dextran | 80/20 | 14 | CTAB | 2 | 7.42 | | 8.67 | | Paracetamol |
| 16 | Dextran | 80/20 | 14 | CTAB | 2 | 6.79 | 10.22 | 18.57 | 0.06 | Rose Bengal |
| 17 | Dextran | 80/20 | 14 | CTAB | 2 | 8.99 | 8.41 | 7.34 | 0.06 | Methyl Orange |
| 18 | Dextran | 80/20 | 14 | CTAB | 2 | 9.62 | 13.07 | 35.72 | 0.05 | Rhodamine |
| 19 | PVA | 80/20 | 10 | Brij 30 | 10 | 12.13 | 6.02 | 40.11 | 0.06 | None |
| 20 | PVA | 80/20 | 14 | SDS | 2 | 10.56 | 7.13 | 20.44 | 0.05 | None |
| 21 | PVA | 80/20 | 10 | Tween 40 | 10 | 2.71 | 1.98 | 38.33 | 0.18 | None |

Notes:
Dextran obtained from Fluka ($M_r$ = 110,000 g/mol). PVA = poly(vinyl alcohol), obtained from Aldrich ($M_w$ = 10,000 g/mol, 80% hydrolyzed)

Sample 1 was prepared by freeze drying a 14% w/v aqueous solution of dextran in the absence of any surfactant. No CO$_2$ emulsion template was present and the structure does not show emulsion-templated porosity as illustrated in FIG. 1. The bulk polymer density of sample 1 was found to be 0.30 g/cm$^3$. Pore volume was 2.13 cm$^3$/g. The median pore diameter was 4.07 microns.

Figure 2:
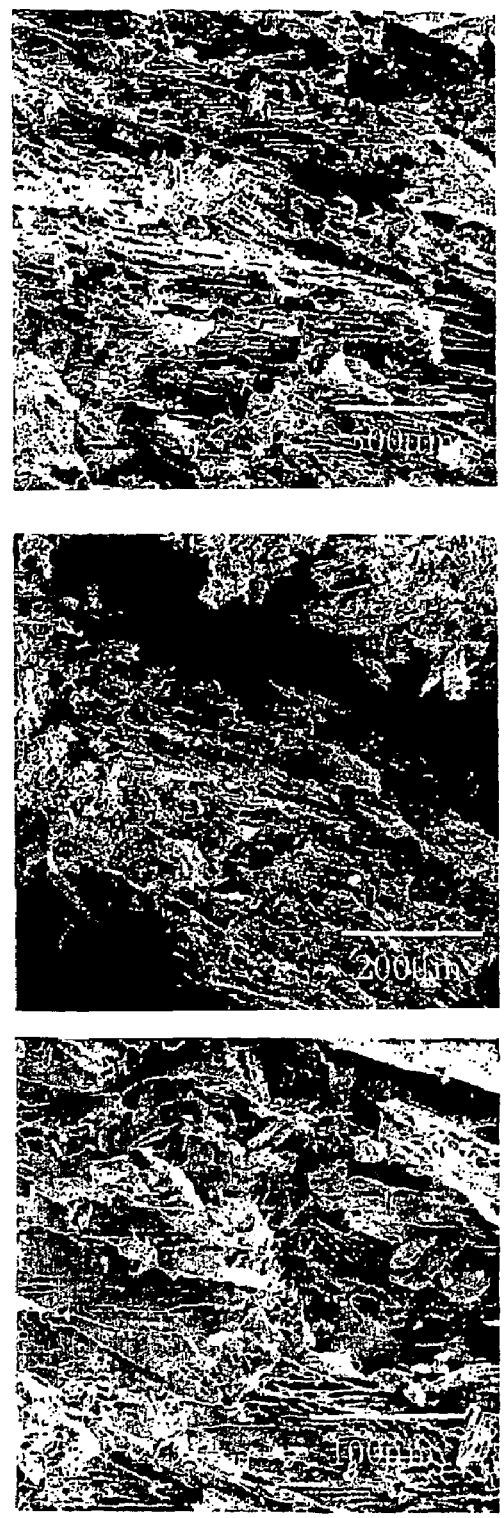
FIG. 2 is an electron micrograph at three different magnifications of a porous material produced in Sample 2 in accordance with the present invention.

Sample 2 was prepared by freeze drying a 14% W/v aqueous solution of dextran mixed with 2% w/v CTAB surfactant and the structure is shown in FIG. 2. No CO$_2$ emulsion template was present and the structure does not show emulsion-templated porosity. Bulk polymer density was found to be 0.37 g/cm$^3$ and the pore volume to be 1.80 cm$^3$/g, whilst the median pore diameter was found to be 4.83 microns.

Figure 3:
FIG. 3 is an electron micrograph at three different magnifications of a porous material produced in Sample 3 in accordance with the present invention.
Figure 3:
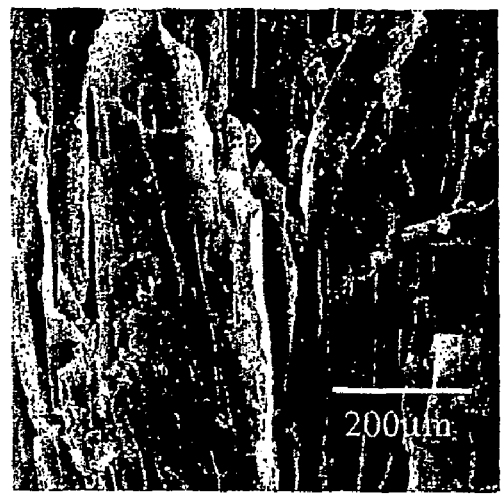
Figure 3:
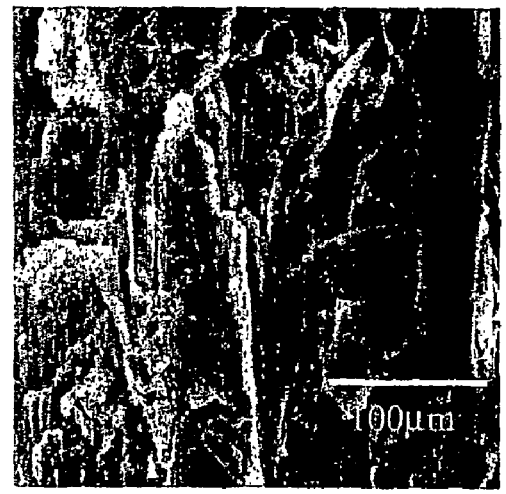

Sample 3 was prepared by freeze drying a 14% w/v aqueous solution of dextran mixed with 20% w/v CTAB surfactant and the structure is shown in FIG. 3. No CO$_2$ emulsion template was present and the structure does not show emulsion-templated porosity. The bulk polymer density was found to be 0.20 g/cm$^3$, the pore volume was found to be 3.43 cm$^3$/g and the median pore diameter 6.1 microns.

Figure 4:
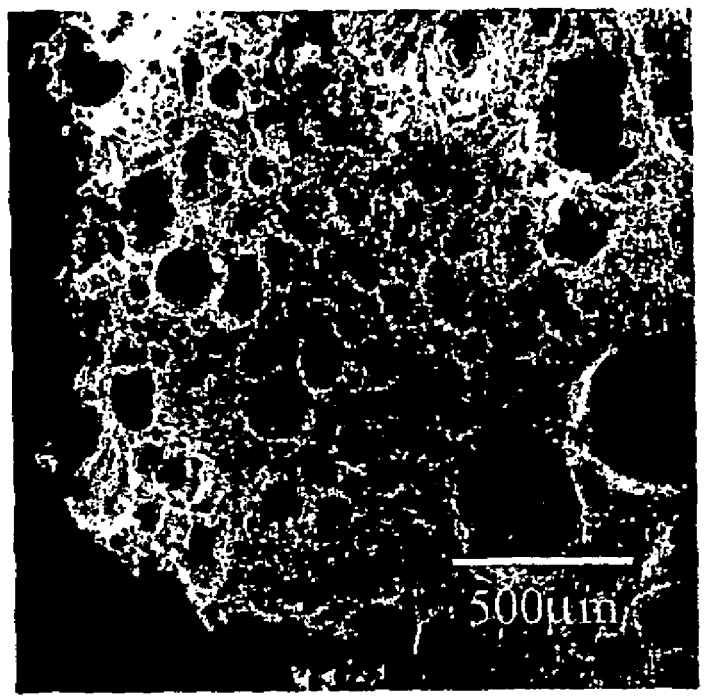
FIG. 4 is an electron micrograph at three different magnifications of a porous material produced in Sample 5 in accordance with the present invention.
Figure 4:
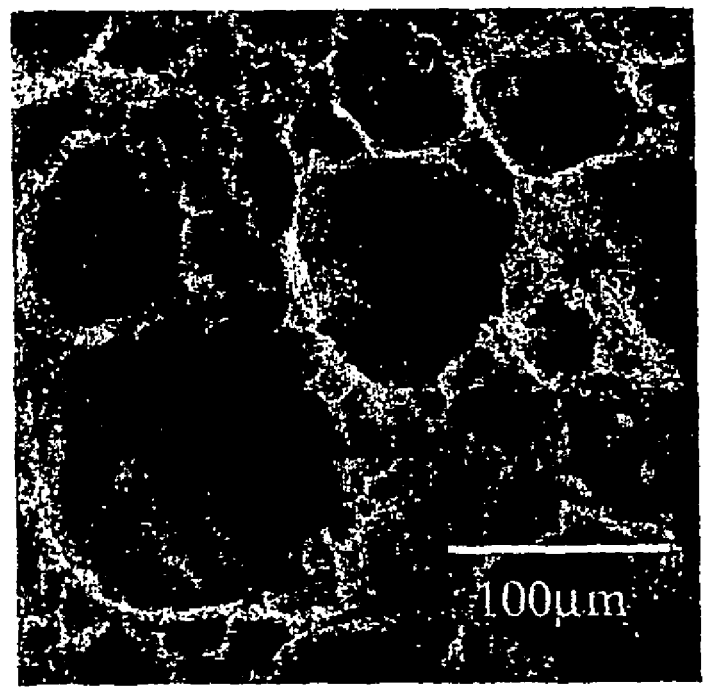

Sample 5 was prepared by freeze drying a 8% w/v aqueous solution of dextran mixed with 20% w/v CTAB surfactant in the presence of 80% v/v CO$_2$ emulsion template with respect to the aqueous phase and the structure is shown in FIG. 4. The structure clearly shows emulsion-templated porosity. The bulk polymer density was found to be 0.06 g/cm$^3$ and the pore volume 11.68 cm$^3$/g. The median pore diameter was found to be 18.68 microns.

Figure 5:
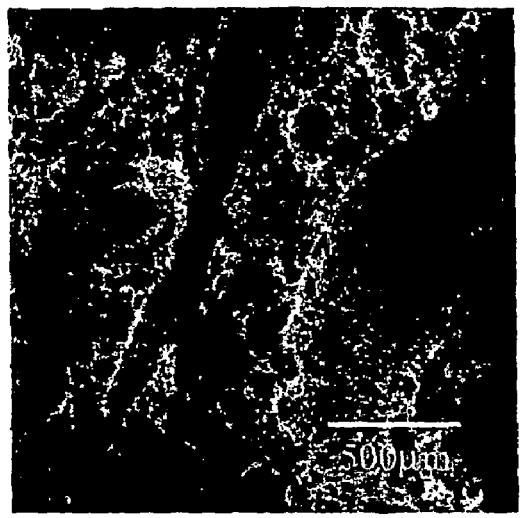
FIG. 5 is an electron micrograph at three different magnifications of a porous material produced in Sample 7 in accordance with the present invention.
Figure 5:
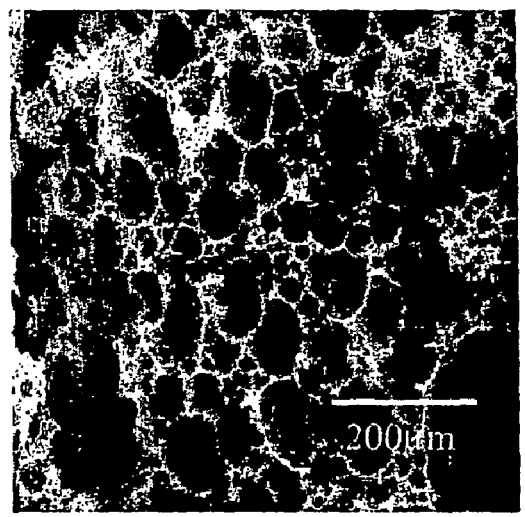
Figure 5:
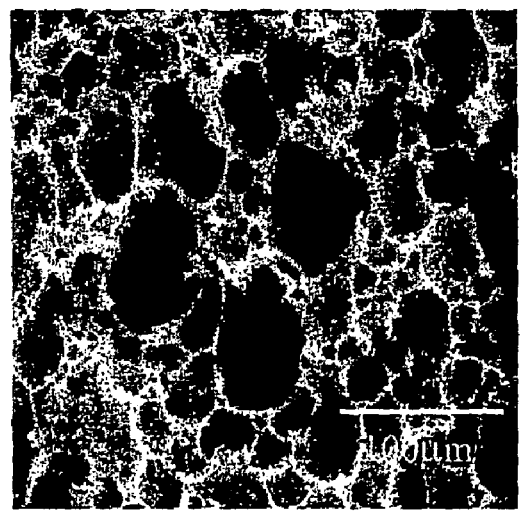

Sample 7 was prepared by freeze drying a 14% w/v aqueous solution of dextran mixed with 2% w/v CTAB surfactant in the presence of 80% v/v CO$_2$ emulsion template with respect to the aqueous phase and the structure is shown in FIG. 5. The structure clearly shows emulsion-templated porosity. The bulk polymer density was found to be 0.05 g/cm$^3$, whilst the pore volume was found to be 14.22 cm$^3$/g. The structure had a median pore diameter of 15.24 microns.

Figure 6:
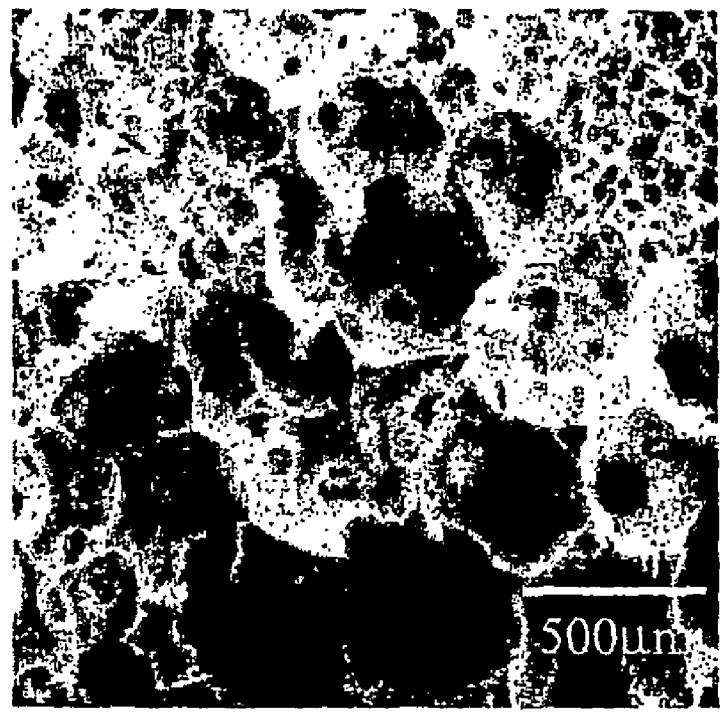
FIG. 6 is an electron micrograph at two different magnifications of a porous material produced in Sample 16 in accordance with the present invention.
Figure 6:
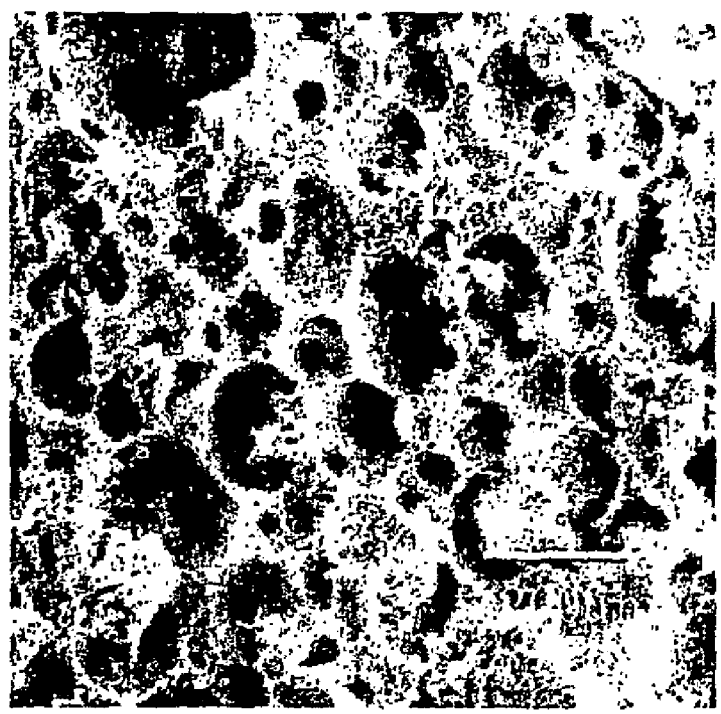

Sample 16 was prepared by freeze drying a 14% w/v aqueous solution of dextran mixed with 2% w/v CTAB surfactant in the presence of 80% v/v CO$_2$ emulsion template with respect to the aqueous phase and the structure is shown in FIG. 6. The structure clearly shows emulsion-templated porosity. A water-soluble dye, Rose Bengal, was dissolved in the aqueous phase and is entrapped in the walls of the polymer structure. The bulk polymer density was found to be 0.06 g/cm$^3$, the pore volume 10.22 cm$^3$/g and the median pore diameter 18.57 microns.

Figure 7:
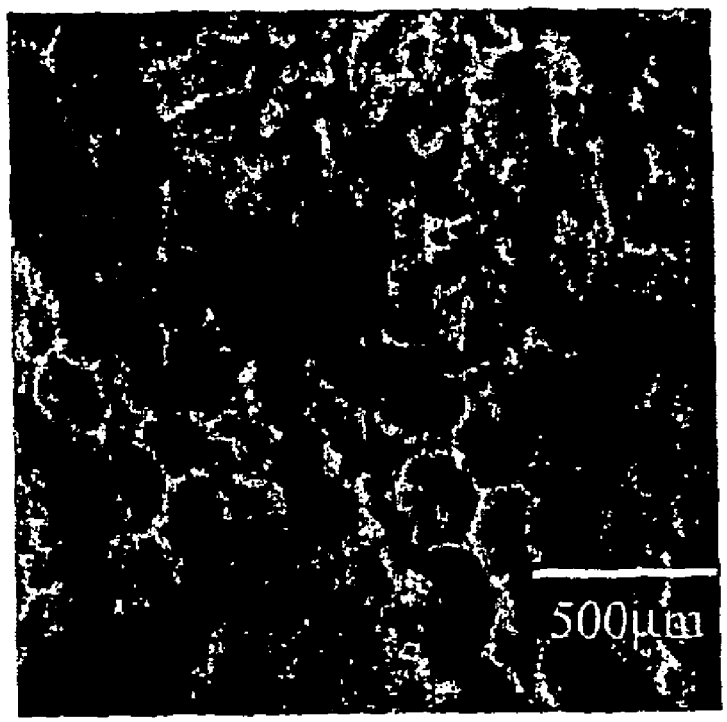
FIG. 7 is an electron micrograph at two different magnifications of a porous material produced in Sample 18 in accordance with the present invention.
Figure 7:
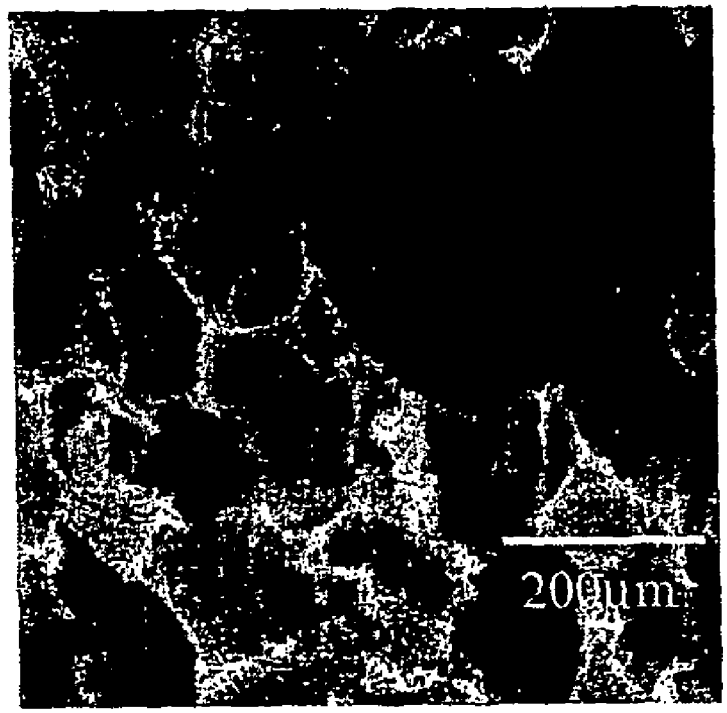

Sample 18 was prepared by freeze drying a 14% w/v aqueous solution of dextran mixed with 2% w/v CTAB surfactant in the presence of 80% v/v CO$_2$ emulsion template with respect to the aqueous phase and the structure is shown in FIG. 7. The structure clearly shows emulsion-templated porosity. A water-soluble dye, Rhodamine, was dissolved in the aqueous phase and is entrapped in the walls of the polymer structure. Bulk polymer density was found to be 0.05 g/cm$^3$, the pore volume 13.07 cm$^3$/g and the median pore diameter 35.72 microns.

Figure 8:
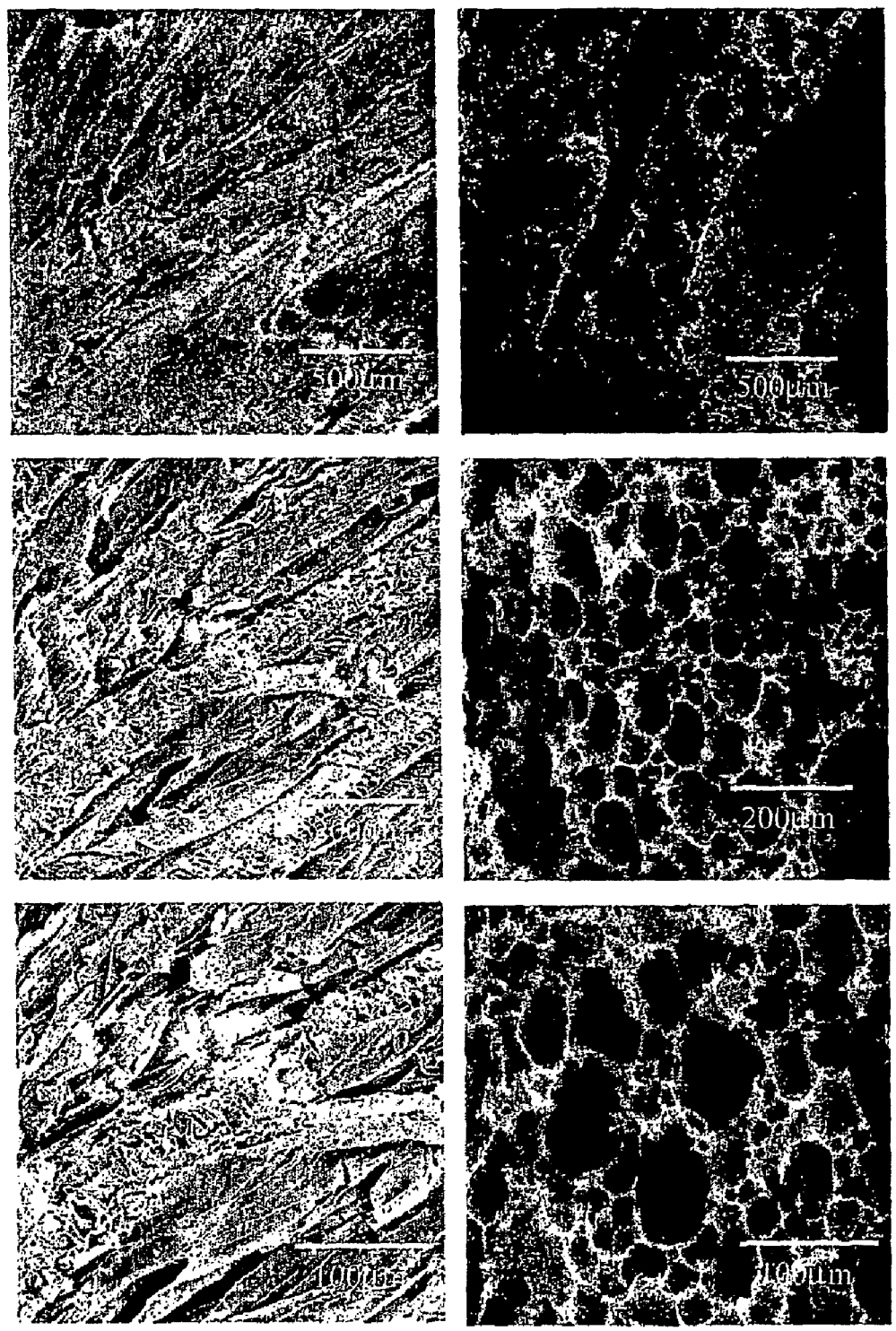
FIG. 8 is an electron micrograph at three different magnifications of a porous materials showing a direct comparison between Sample 2 and Sample 7.

FIG. 8 shows a direct comparison between the structures formed in Sample 2 and Sample 7 (formed without and with the CO$_2$ emulsion template respectively). The presence of the CO$_2$ emulsion had led to a much higher pore volume (14.22 cm$^3$/g vs 1.80 cm$^3$/g) and a larger pore size (15.24 microns vs 4.83 microns). The emulsion templated material (Sample 7) shows a highly interconnected pore structure that is absent in the material prepared without the emulsion (Sample 2).

Figure 9:
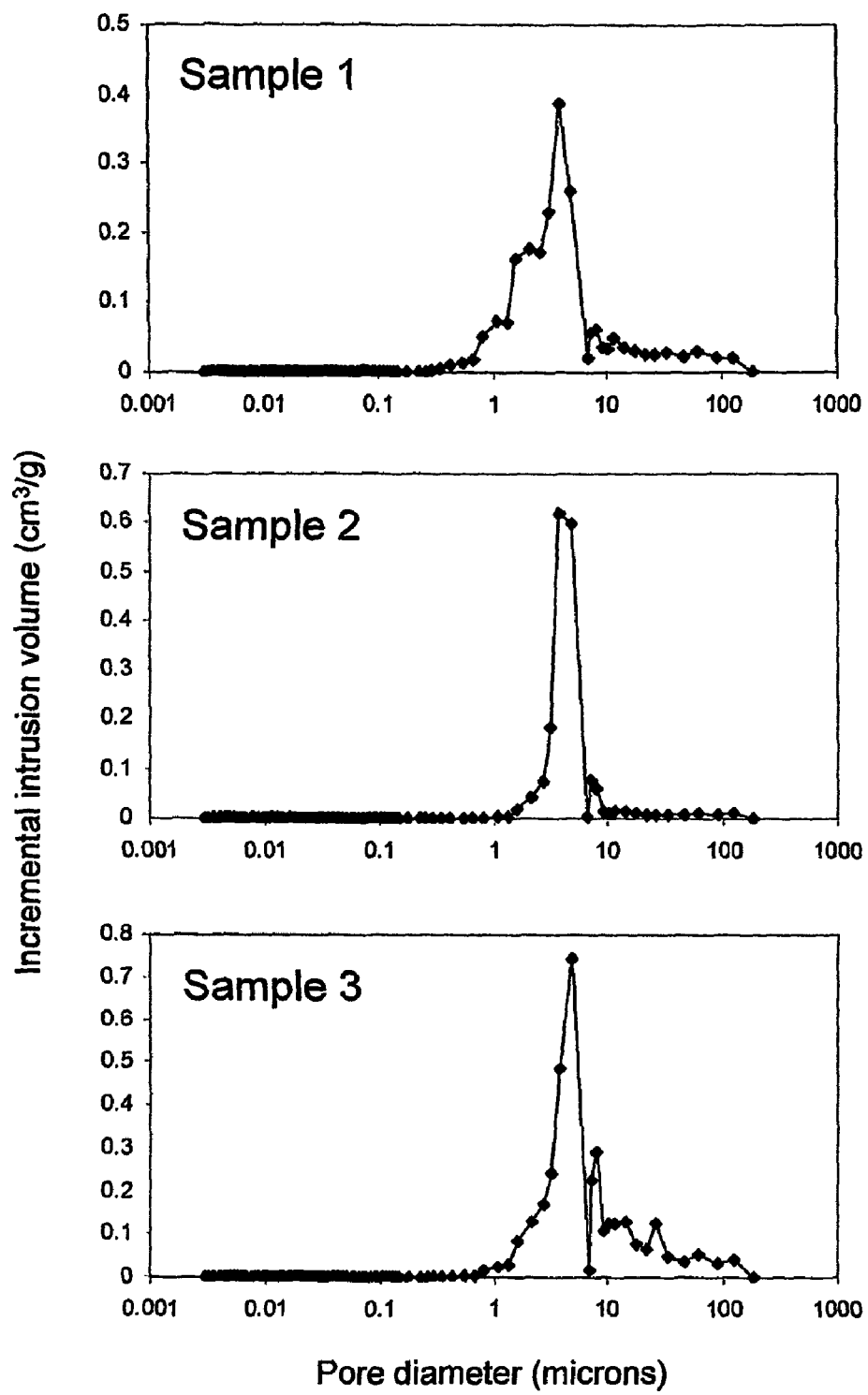
FIG. 9 shows mercury intrusion porosimetry data for dextran samples prepared by freeze-drying of aqueous solutions in the absence of any $CO_2$ emulsion template for samples 1, 2 and 3.

Samples 1, 2 and 3 (prepared without any emulsion template) have an average pore size range from about 4-6 microns and total pore volumes in the range between 1.8-3.4 cm$^3$/g and this data is shown in the graphs in FIG. 9.

Figure 10:
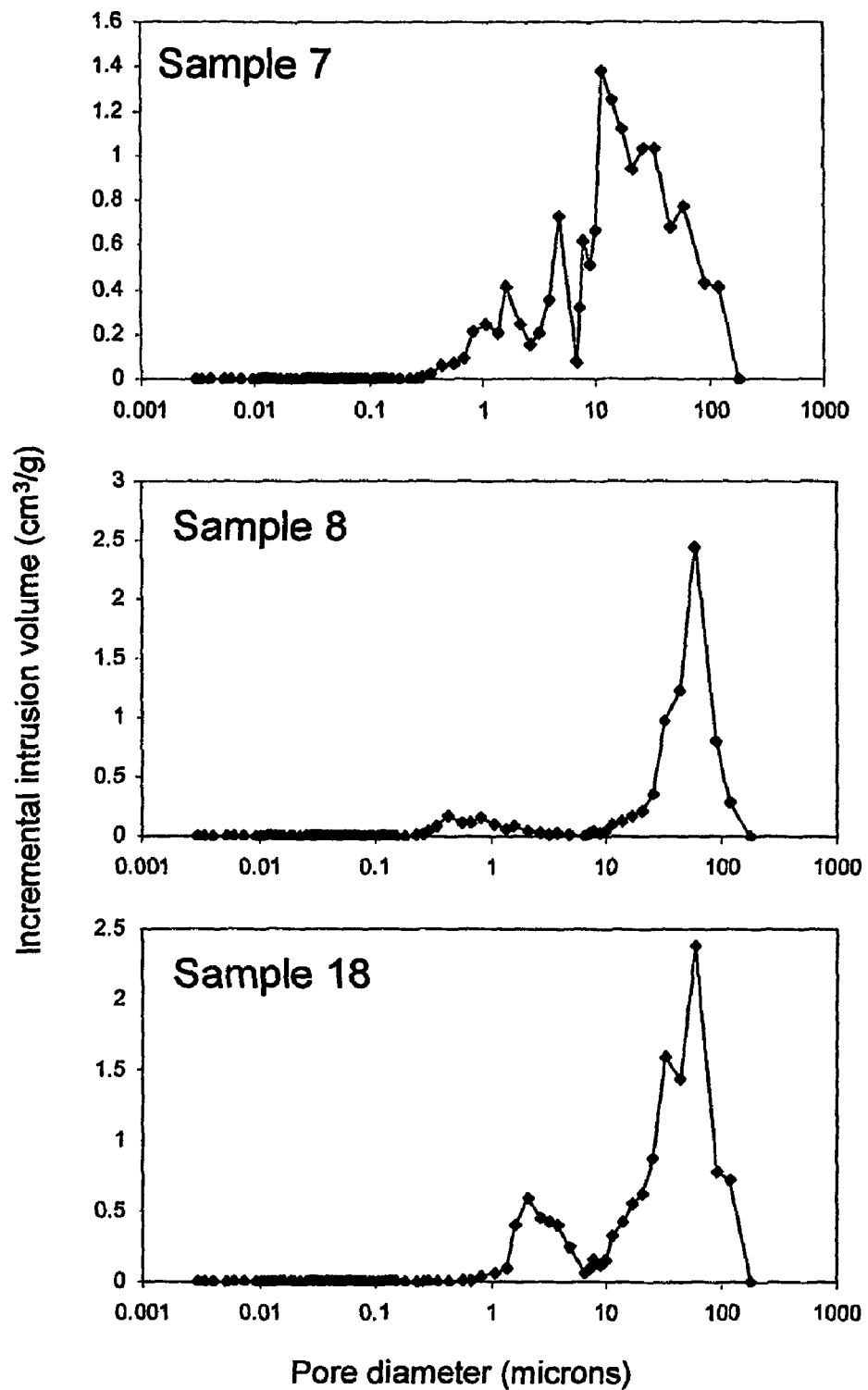
FIG. 10 shows mercury intrusion porosimetry data for dextran samples prepared by freeze-drying of aqueous solutions in the presence of a 80% v/v $CO_2$ emulsion template for samples 7, 8 and 18.

FIG. 10 illustrates the mercury intrusion porosimetry data for dextran samples prepared by freeze-drying of aqueous solutions in the presence of a 80% v/v CO$_2$ emulsion template in Samples 7, 8 & 18. Average pore sizes range from about 15-55 microns and total pore volumes range between 8-14 cm$^3$/g.

Figure 11:
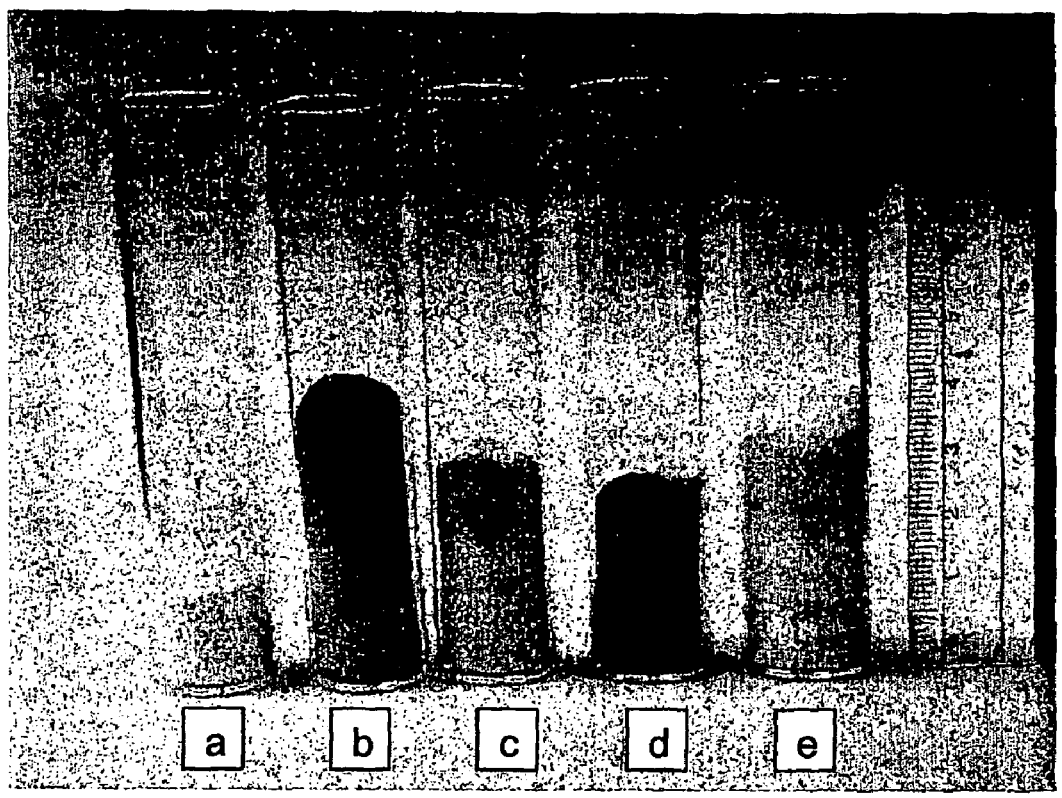
FIG. 11 is a photograph showing various templated dextran materials in accordance with the present invention.

FIG. 11 is a photograph showing various freeze-dried dextran materials (scale at right of photograph is in centimetres). Samples are, from left to right: (a) Sample 2, prepared without any CO$_2$ emulsion template; (b) Sample 16, prepared using 80% v/v CO$_2$ emulsion template and entrapping a water-soluble Rhodamine dye; (c) Sample 17, prepared using 80% v/v CO$_2$ emulsion template and entrapping a water-soluble dye, Methyl Orange; (d) Sample 18, prepared using 80% v/v $CO_2$ emulsion template and entrapping a water-soluble dye, Rose Bengal; (e) Sample 11, prepared using 80% v/v $CO_2$ emulsion template without any additional dopant molecules.

Figure 12:
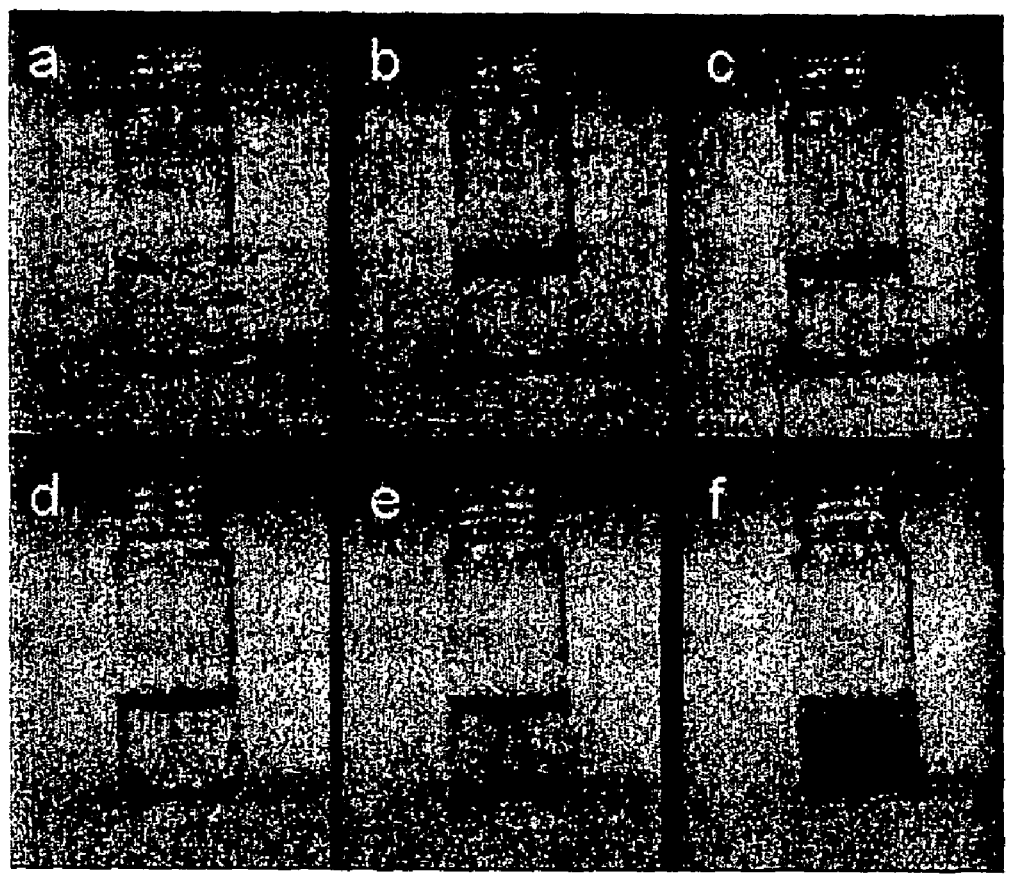
FIG. 12 shows photographs illustrating the rapid dissolution of a small piece (~50 mg) of Sample 18 in pure water.

FIG. 12 is a series of photographs showing rapid dissolution of a small piece (~50 mg) of Sample 18 in pure water (approx. 10 cm$^3$) without stirring at 20° C. It was found that the sample dissolves entirely in less than 10 seconds. If the solution is gently swirled, the dye becomes homogeneously distributed throughout the aqueous phase (photograph f).

Figure 13:
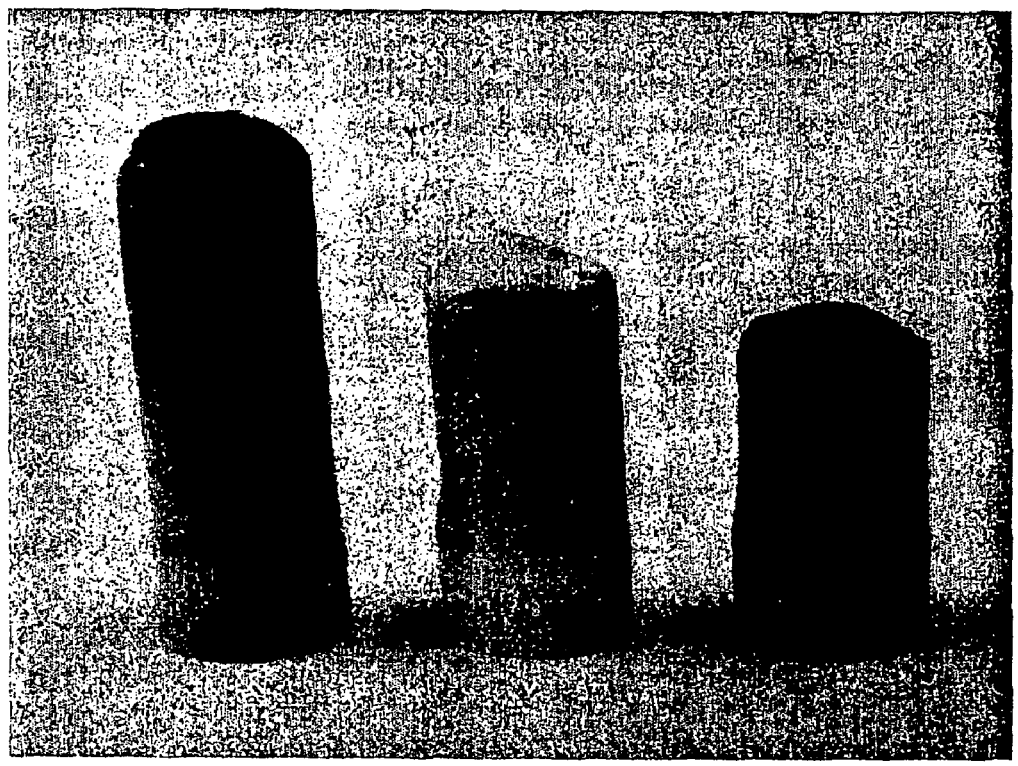
FIG. 13 shows close up photographs of emulsion-templated samples containing water-soluble dyes in accordance with the present invention.

FIG. 13 shows close up photographs of moulded, monolithic emulsion-templated samples containing water-soluble dyes. The samples are, left to right, Samples 16, 17 & 18.

The clear emulsion-templated porosity in the samples produced using $CO_2$ suggests that the emulsions remained stable upon freezing. Analysis by scanning electron microscopy (SEM) showed that the presence of $CO_2$ in the starting emulsion had a significant affect on the nature of the porosity contained within the samples (see comparison made in FIG. 8). The samples made without $CO_2$, (FIGS. 1, 2 and 3) showed plate-like porosity, whereas the samples made with $CO_2$ (FIGS. 4, 5, 6, and 7) showed more spherical porosity. Materials made with dextran using CTAB as a surfactant (FIGS. 4, 5, 6, and 7) showed spherical voids where the individual droplets of the $CO_2$ have been templated. The porosity in these samples was highly interconnected. The average pore diameter, the total pore volume (i.e., intrusion volume), and the bulk density for the samples was investigated using mercury intrusion porosimetry. The emulsion-templated samples were much more highly porous than those produced without the emulsion-template. FIGS. 9 and 10 show intrusion porosimetry data for dextran samples prepared without emulsion template (FIG. 9) and with emulsion template (FIG. 10), respectively. These figures (and the respective SEM images) show clearly that the median pore diameter is much larger in the templated materials due to the presence of emulsion-templated pores.

The invention claimed is:

1. A method for producing a water-soluble porous, polymeric material comprising the steps of:
    (a) providing a C/W emulsion comprising an aqueous phase, a matrix building material in the form of a water-soluble polymeric material, a surfactant and a liquid $CO_2$ phase;
    (b) at least partially freezing the aqueous phase;
    (c) gasifying $CO_2$ from the liquid $CO_2$ phase to produce an intermediate porous material;
    (d) venting the gasified $CO_2$ from the intermediate porous material; and
    (e) freeze drying the intermediate porous material at least substantially to remove the aqueous phase and to form the water-soluble porous material; wherein said water-soluble polymeric material is one or more chosen from the group consisting of water-soluble polysaccharides and water-soluble vinyl polymers, and is substantially free of cross-linking such that said water-soluble porous material is able to substantially fully dissolve in water at 20° C.

2. A method for producing a porous material as claimed in claim 1, wherein the emulsion further comprises a dopant.

3. A method for producing a porous material as claimed in claim 2, wherein the dopant is substantially water-soluble.

4. A method for producing a porous material as claimed in claim 2, wherein the dopant is selected from one or more of the following dopants: pharmaceutical actives, pharmaceutical salts, enzymes, dyes, oxidising agents, reducing agents, cleaning agents, reagents for organic synthesis, agrochemicals, fabric softeners, clothes care agents, bleaches, flavours, fragrances, vitamins or nutraceuticals, metal nanoparticles (e.g., metal hydrosols), inorganic nanoparticles, biological polymers (e.g., DNA, RNA), growth factors/cofactors, and live cells (e.g., stem cells).

5. A method for producing a porous material as claimed in claim 1, wherein a substantially water-soluble inorganic or organic additive is additionally used.

6. A method for producing a porous material as claimed in claim 5, wherein the additive is selected from one or more of the following additives: partially hydrolysed silica precursors (i.e., a silica sol), other alkoxide sols, hydroxyapatite salts, and sodium silicate.

7. A method for producing a porous material as claimed in claim 1, wherein the water-soluble polymeric material is selected from one or more of the following group of materials: poly(vinyl alcohol) and dextran.

8. A method for producing a porous material as claimed in claim 1, wherein the temperature of the emulsion is reduced to a temperature in the range of −5° C. to −30° C.

9. A method for producing a porous material as claimed in claim 1, wherein the $CO_2$ is gasified by means of depressurisation of the intermediate porous material.

10. A method for producing a porous material as claimed in claim 1, wherein the surfactant is selected from one or more of the following list of surfactant: CTAB (cetyltrimethylammonium bromide), SDS (sodium dodecyl sulphate), pluronic surfactants, Brij 30 and Tween 40.

11. A method for producing a porous material as claimed in claim 1, wherein the matrix building material is contained within the aqueous phase of the emulsion.

12. A method for producing a porous material as claimed in claim 1, wherein the constituents of the emulsion are in the following quantities: the matrix building material is in the range of 5-20% w/v and the surfactant is in the range of 5-20% w/v in respect of $H_2O$ and the $CO_2$ is in the range of 65-95% v/v.

13. A method for producing a porous material as claimed in claim 1, wherein the porous material is produced in the form of a monolithic block.

14. A method for producing a porous material as claimed in claim 1, wherein the porous material is produced in the form of porous particles or beads.

15. A method for producing a porous material as claimed in claim 1, wherein the emulsion further comprises an active ingredient for incorporation into the porous material.

16. A method for producing a porous material as claimed in claim 15, wherein the active ingredient is selected from one or more from the following group; pharmaceutical actives, pharmaceutical salts, enzymes, dyes, oxidising agents, reducing agents, cleaning agents, reagents for organic synthesis, agrochemicals, fabric softeners, clothes care agents, bleaches, flavours, fragrances, vitamins or nutraceuticals, metal nanoparticles (e.g., metal hydrosols), inorganic nanoparticles, biological polymers (e.g., DNA, RNA), growth factors/cofactors, and live cells (e.g., stem cells).

17. A water-soluble porous material obtained by the method according to claim 1, wherein the material is characterised by having
    (a) a median pore diameter within the range of 5-100 microns;
    (b) a total pore volume in the range of 8-15 cm$^3$/g when approximately 80% v/v $CO_2$ is used; and
    (c) a bulk density typically in the range 0.02-0.06 g/cm$^3$, and being able to substantially fully dissolve in water at 20° C.

18. A water-soluble porous material according to claim 17, characterised by having substantially no solvent residue remaining in the material that arises from the internal template phase.

19. A water-soluble porous material according to claim 17, being produced in the form of a moulded, monolithic block that substantially conforms to the shape of a vessel in which it is produced.

20. A water-soluble porous material comprising a water-soluble polymer matrix, wherein the water-soluble porous material is produced according to the method of claim 1, and wherein said matrix comprises substantially no residual organic solvent.

21. A water-soluble porous material according to claim 20 obtainable by a method which utilises substantially no organic solvent, hence the matrix being substantially free from any residual organic solvent component.

22. A water-soluble porous material according to claim 20 comprising surfactant moieties entangled with the polymeric matrix.

23. A water-soluble porous material according to claim 22, wherein the presence of surfactant moieties results from the formation of the porous material from a C/W emulsion comprising the surfactant moieties.

24. A water-soluble porous material as claimed in claim 20, wherein the material is used for one or more of the following applications: biomaterials, food materials, DNA storage, controlled release matrices, agrochemical release, reagent release (e.g., for chemical reactions), molecular separations and diagnostic reagent release.

* * * * *

UNITED STATES PATENT AND TRADEMARK OFFICE
CERTIFICATE OF CORRECTION

PATENT NO.         : 8,357,728 B2                                                            Page 1 of 1
APPLICATION NO. : 10/566873
DATED              : January 22, 2013
INVENTOR(S)        : Butler et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1404 days.

Signed and Sealed this

First Day of September, 2015

Michelle K. Lee
*Director of the United States Patent and Trademark Office*